(12) United States Patent
Erickson et al.

(10) Patent No.: US 11,075,992 B2
(45) Date of Patent: Jul. 27, 2021

(54) SYSTEM AND METHOD FOR PROVIDING MEDICAL ATTENTION

(71) Applicant: International Business Machines Corporation, Armonk, NY (US)

(72) Inventors: Thomas David Erickson, Minneapolis, MN (US); Clifford A. Pickover, Yorktown Heights, NY (US); Maja Vukovic, New York, NY (US); Komminist Weldemariam, Nairobi (KE)

(73) Assignee: International Business Machines Corporation, Armonk, NY (US)

( * ) Notice: Subject to any disclaimer, the term of this patent is extended or adjusted under 35 U.S.C. 154(b) by 954 days.

(21) Appl. No.: 15/222,574

(22) Filed: Jul. 28, 2016

(65) Prior Publication Data
US 2018/0028364 A1 Feb. 1, 2018

(51) Int. Cl.
| | |
|---|---|
| A61F 13/04 | (2006.01) |
| B64D 1/18 | (2006.01) |
| H04L 29/08 | (2006.01) |
| A61B 5/00 | (2006.01) |
| A61F 5/058 | (2006.01) |
| A61B 5/107 | (2006.01) |
| G05D 1/00 | (2006.01) |
| A61F 13/00 | (2006.01) |
| G16H 50/20 | (2018.01) |

(Continued)

(52) U.S. Cl.
CPC ............ *H04L 67/12* (2013.01); *A61B 5/0013* (2013.01); *A61B 5/0033* (2013.01); *A61B 5/0036* (2018.08); *A61B 5/1079* (2013.01); *A61B 5/441* (2013.01); *A61B 5/4504* (2013.01); *A61B 5/4887* (2013.01); *A61B 5/6887* (2013.01); *A61B 5/7264* (2013.01); *A61F 5/05841* (2013.01); *A61F 13/00051* (2013.01);

(Continued)

(58) Field of Classification Search
CPC ........ A61F 2013/0011; A61F 15/05841; A61F 13/04; A61F 5/05841; A61F 5/013; B64C 39/024; B64C 2201/128; B64C 39/02; G06T 7/00; G06F 19/30; G06F 19/3418; G16H 40/67; G16H 20/40; H04L 67/12; A61B 90/361; A61B 2034/105; A61B 2576/02; A61B 5/4504; B64D 1/18; G05D 1/0094; A62D 1/0071
See application file for complete search history.

(56) References Cited

U.S. PATENT DOCUMENTS 3,581,826 A * 6/1971 Dougan ............... A62D 1/0071
169/15
6,252,598 B1 6/2001 Segen
(Continued)

FOREIGN PATENT DOCUMENTS

KR 101566341 B1 * 11/2015 ............. B64C 39/02

OTHER PUBLICATIONS

Abstract and description of KR101566341 (translations) (Year: 2015).*

(Continued)

*Primary Examiner* — Brian E Pellegrino
(74) *Attorney, Agent, or Firm* — Shimon Benjamin; Otterstedt, Wallace & Kammer, LLP (57) ABSTRACT

Ameliorative actions are taken using a system equipped with sensors and equipment for attending to a patient. Operation of the system is controlled at a remote site or alternatively at the location of an injury. Injury assessment and the patient's affective and/or cognitive state may be facilitated through the analysis of data obtained by the sensors.

9 Claims, 2 Drawing Sheets

(51) Int. Cl.
    *G16H 20/40*     (2018.01)
    *G16H 30/40*     (2018.01)
    *G16H 50/70*     (2018.01)
    *G16H 20/13*     (2018.01)

(52) U.S. Cl.
    CPC ........... *A61F 13/04* (2013.01); *G05D 1/0094* (2013.01); *G16H 20/40* (2018.01); *G16H 30/40* (2018.01); *G16H 50/20* (2018.01); *G16H 50/70* (2018.01); *H04L 67/10* (2013.01); *H04L 67/18* (2013.01); *A61B 5/0022* (2013.01); *A61B 5/7275* (2013.01); *B64D 1/18* (2013.01); *G16H 20/13* (2018.01)

(56) References Cited

U.S. PATENT DOCUMENTS

| | | | |
|---|---|---|---|
| 8,526,700 B2* | 9/2013 | Isaacs | G06F 19/321 |
| | | | 382/131 |
| 9,140,526 B1 | 9/2015 | Calvert | |
| 9,307,383 B1* | 4/2016 | Patrick | B64C 39/024 |
| 10,155,587 B1* | 12/2018 | Tang | B64C 39/024 |
| 2002/0090146 A1 | 7/2002 | Heger et al. | |
| 2002/0130200 A1 | 9/2002 | Hurray et al. | |
| 2006/0079819 A1 | 4/2006 | Evans et al. | |
| 2006/0271407 A1* | 11/2006 | Rosenfeld | G06F 19/3418 |
| | | | 434/262 |
| 2013/0324897 A1 | 12/2013 | Martin | |
| 2018/0134387 A1* | 5/2018 | Kovac | B64D 1/18 |
| 2019/0023392 A1* | 1/2019 | Micros | B64C 39/024 |

OTHER PUBLICATIONS

Hunt, Graham et al., "3D Printing with Flying Robots", 2014 IEEE international Conference on Robotics and Automation, Hong Kong Cnvention and Exhibition Center, May 31-Jun. 7, 2014, Hong Kong, China 8 pages. (Year: 2014).*

Martin, Kevin D., Spray Polyurethan Foam Splint: FastCast, Medical Technology Transfer, US Army, Nov. 18, 2010, http://technologytransfer.amedd.army.mil/assets/docs/abstracts/factsheet_FastCast.pdf, p. 1.

* cited by examiner

SYSTEM AND METHOD FOR PROVIDING MEDICAL ATTENTION

FIELD

The present disclosure relates to the identification of injured persons or animals and the immobilization of injured limbs through the application of foam using unmanned aerial vehicles (UAVs).

BACKGROUND

Unmanned aerial vehicles have been developed for a number of uses, including surveillance, aerial filming, agricultural applications, and recreation. They are commonly referred to as drones. UAV designs include fuselage/wing assemblies resembling planes as well as helicopter and quadcopter configurations. Sensors such as gyroscopes, accelerometers, altimeters, GPS modules, cameras and/or payload monitors may be incorporated within UAVs. Gimbals may be used to mount cameras in UAVs. Radio signals generated by a transmitter/receiver, a smartphone, a tablet or other device can be used to control a UAV. UAVs can be designed to operate partially or completely autonomously. Functions such as hovering and returning to home can, for example, be provided autonomously. Data obtained by UAVs can be stored onboard using, for example, SD cards, or transmitted wirelessly. UAVs have been employed in the agriculture industry for purposes such as monitoring livestock and crops as well as crop dusting.

Orthopedic injuries such as bone fractures, sprains, and damaged ligaments and/or tendons often require prompt medical attention and stabilization to avoid further damage to the injured extremity and pain experienced by a patient. In remote settings, however, it is difficult to provide prompt and efficient medical treatment. Immediate and intense pain followed by numbness and tingling are among the symptoms of a bone fracture. Swelling, tenderness, bruising and possible blood loss are among the complications that may arise from a fractured limb. Deformation of the limb and decreased range of motion may further be observed. Current techniques often require multiple steps and components, thereby prolonging pain, swelling, and potential secondary injury.

SUMMARY

Embodiments of the present disclosure provide a an unmanned aerial vehicle having video capability and a spray nozzle for creating a foam splint.

A method for assisting a patient entails obtaining an unmanned aerial vehicle including a payload including one or more materials for forming a polymer foam, a dispenser for dispensing the one or more materials in the payload, and one or more sensors. The method further includes flying the unmanned aerial vehicle to a location in proximity to a patient, identifying the patient at the location using the one or more sensors, and dispensing the one or more materials for forming the polymer foam on a limb of the patient, thereby forming a foam splint on the limb.

Additional aspects of the disclosure are directed to a system for assisting an injured patient. The system includes an unmanned aerial vehicle having a payload including one or more materials for forming a polymer foam, a dispenser for dispensing the one or more materials in the payload, and one or more sensors. A processor is configured for processing outputs from the one or more sensors to identify a patient at a location using the one or more sensors, obtain physical characteristics data relating to the patient based on an output of the one or more sensors, and determine whether it is likely that a limb of the patient is injured based on the physical characteristics data. An actuator is provided for actuating the dispenser.

BRIEF DESCRIPTION OF THE DRAWINGS

These and other features, aspects, and advantages of the present invention will become better understood with regard to the following description, appended claims, and accompanying drawings where:

DETAILED DESCRIPTION

The subject matter of the instant application will be described with reference to illustrative embodiments. For this reason, numerous modifications can be made to these embodiments and the results will still come within the scope of the invention. No limitations with respect to the specific embodiments described herein are intended or should be inferred.

Figure 1:
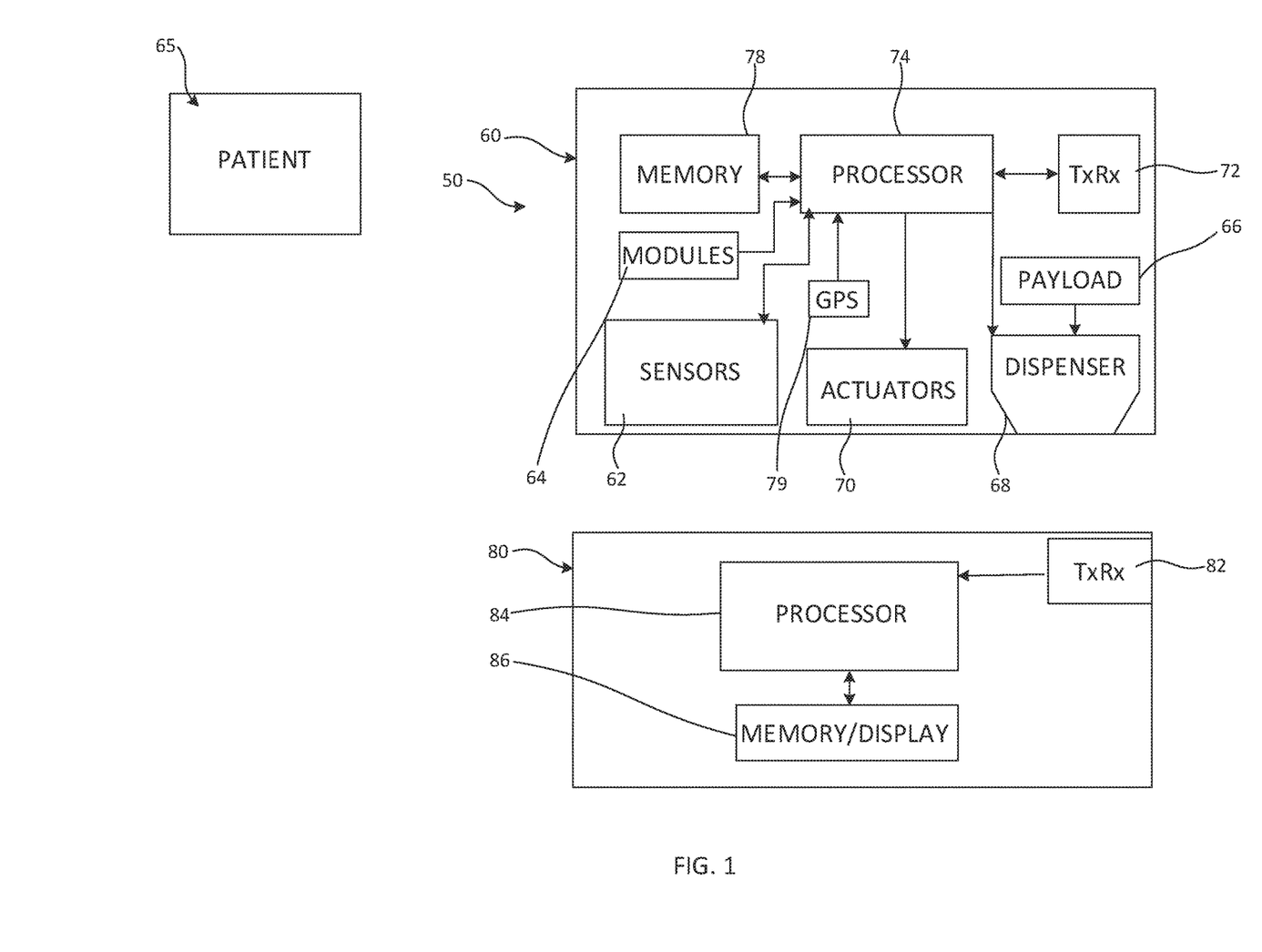
FIG. 1 is a schematic diagram of a system for identifying injured persons and treating the injuries using an unmanned aerial vehicle.

A system 50 is disclosed herein that includes an unmanned aerial vehicle (UAV) 60 including one or more sensors 62 for locating a person or animal (patient 65) with an injury and detecting or inferring the nature of the injury. The UAV 60 includes a payload 66 including material(s) for immobilizing an injured portion of a body, for example the components of a foamable composition, and one or more delivery devices (e.g. nozzle 68) such as a spray nozzle for applying the material(s) to the body. Based on the detection or inference of the injury, the UAV is further enabled in some embodiments to take further amelioration action with respect to the injury, such as the application of antibiotics, anesthetics or other material(s). The payload 66 accordingly includes a plurality of compartments in some embodiments. Actuators 70 within the UAV control functions such as the dispensing of material(s) from the payload 66 by the delivery device 68. The actuators further control other operations of the UAV, such as speed controllers and other mechanisms affecting flight.

The UAV is configured for detecting or inferring an injury such as a bone fracture within a limb or other type of injury requiring immobilization. Information detected by the sensors 62 is processed using programs stored in the memory 78 or a module 64 configured for analyzing raw data from one or more sensors. Injury detection may be based on visual identification using deep neural nets, acoustic analysis, and/or other detected information. Visual identification can be assisted by a wireless transmitter/receiver Tx/Rx 72 from the UAV to a remote observer (e.g. physician or paramedic) and/or stored in a memory 78 within the UAV for analysis conducted within the UAV and/or the remote observer. In some embodiments, a high-definition video feed is provided to a remote professional. In some embodiments, the UAV includes an internal processor 74 that facilitates determination of whether there is an injury that should be immobilized and/or addressed with other ameliorative actions, possibly referencing analytics models and injury databases stored on the UAV or remotely. In other embodiments, processing is also conducted at a remote location and instructions are provided to the UAV from the remote location. Neural nets can, for example, be used to help identify injuries either alone or in association with communications from the patient that are transmitted by the UAV to a remote healthcare professional.

The exemplary UAV 60 includes geolocation features such as tracking hardware and software 79 that enable, for example, GPS tracking. Recorded GPS data can be stored in the memory 78 and/or transmitted by the wireless transmitter/receiver Tx/Rx 72 to a central location. Based on the detected injury, appropriate type(s) and amount(s) of material(s) to be administered can be determined as described further below. In some embodiments, the UAV can identify individuals and/or injuries using a unique identification that may be applied to the patient's body (e.g. barcode, color pattern). Patients provided with RFID tags or such other identifiers allows them to be identified and monitored through time by the UAV-based system. The UAV may further incorporate devices for emitting radiation of selected wavelengths incorporated with the actuators 70 or elsewhere. The emission of light in the visible spectrum can facilitate diagnosis of injuries and patient identification where ambient light is insufficient. Emission of radiation of other wavelengths can be also be used in diagnosing injuries. Patient identification and information relating to pain and/or injuries is communicated by the patient to a healthcare professional via the UAV in some embodiments where the patient or someone nearby is able to communicate audibly and/or through gestures.

The UAV is controlled, at least in part, by a device 80 including a transmitter/receiver 82. The device 80 can be a laptop computer, a smartphone, a tablet, or other suitable device. In addition to the transmitter/receiver 82, the device includes a processor 84 and a memory/display 86. Applications for controlling UAVs using such devices are known to the art. One or both of the device 80 and UAV 60 may include a GPS logger. Time is preferably correlated with GPS log data. It will be appreciated that the system 50 can be employed in conjunction with cloud-based systems that receive, maintain and process information obtained by the UAV, as discussed further below.

The sensors 62 incorporated within the UAV 60 include one or more cameras for obtaining high-definition digital images, acoustic detector(s) such as piezoelectric sensors, back scattering devices, and/or chemical detector(s). High-definition visual images, possibly coupled with audio transmissions by the UAV, can facilitate self-reporting of injuries by a patient and decision-making by healthcare professionals with respect to possible action to be taken by the UAV. Analysis of digital images can alternatively or additionally be conducted electronically. Acoustic detection facilitates analysis of the environment surrounding the site of the injury. This may involve audio or vibration sensors located on the UAV. For example, analog signals detected by an acoustic detector can be amplified and processed to obtain digital signals that are stored in the memory 78, transmitted to the healthcare professional, and/or cause the UAV to take action or refrain from taking action. Speech recognition software incorporated within the UAV can be employed to allow the patient 65 or a nearby individual to provide instructions to the UAV to control selected actions, such as the application of a foam spray and/or discontinuation of spraying. Combinations of visual, audio and/or other types of data (e.g. temperature, chemical) can be employed to increase the confidence level regarding the decision as to whether the UAV should take ameliorative action. Videoanalytic software is incorporated with some embodiments of the UAV to determine whether a detected object is a person and to further identify the torso and limbs of the person and possible injuries to the torso and limbs. The assessment may further include detecting the body temperature of the patient 65 and/or inspecting wounds. The UAV may carry a tuning fork in the payload for use by the patient or nearby individual to increase or decrease the confidence level of an injury diagnosis. While lacking the reliability of sophisticated diagnostic equipment such as MIll machines or 3D imagers, tuning forks may be easily used at an injury site by a patient receiving instructions via the UAV. When the tuning fork is struck, then held in contact with the bone, high-frequency vibrations travel into the bone. A sharp pain may be experienced by the patient if, for example, a stress fracture exists. Based on said assessment and risk management factor(s), the UAV 60 takes amelioration action such as immobilizing an injury by applying a foam cast, applying medication or anesthetics, or taking other actions that benefit the patient. Such action may additionally or alternatively be taken by other UAVs configured for spraying foam on an injured person or applying other remedial substances. The UAV may or may not include processing capability for processing the data obtained by the onboard sensors 62. The UAV optionally transmits video data, acoustical data, physiological data and/or temperature data to a remote server and/or a professional for such processing. FIG. 1 includes a diagram showing an exemplary system 50.

Figure 2:
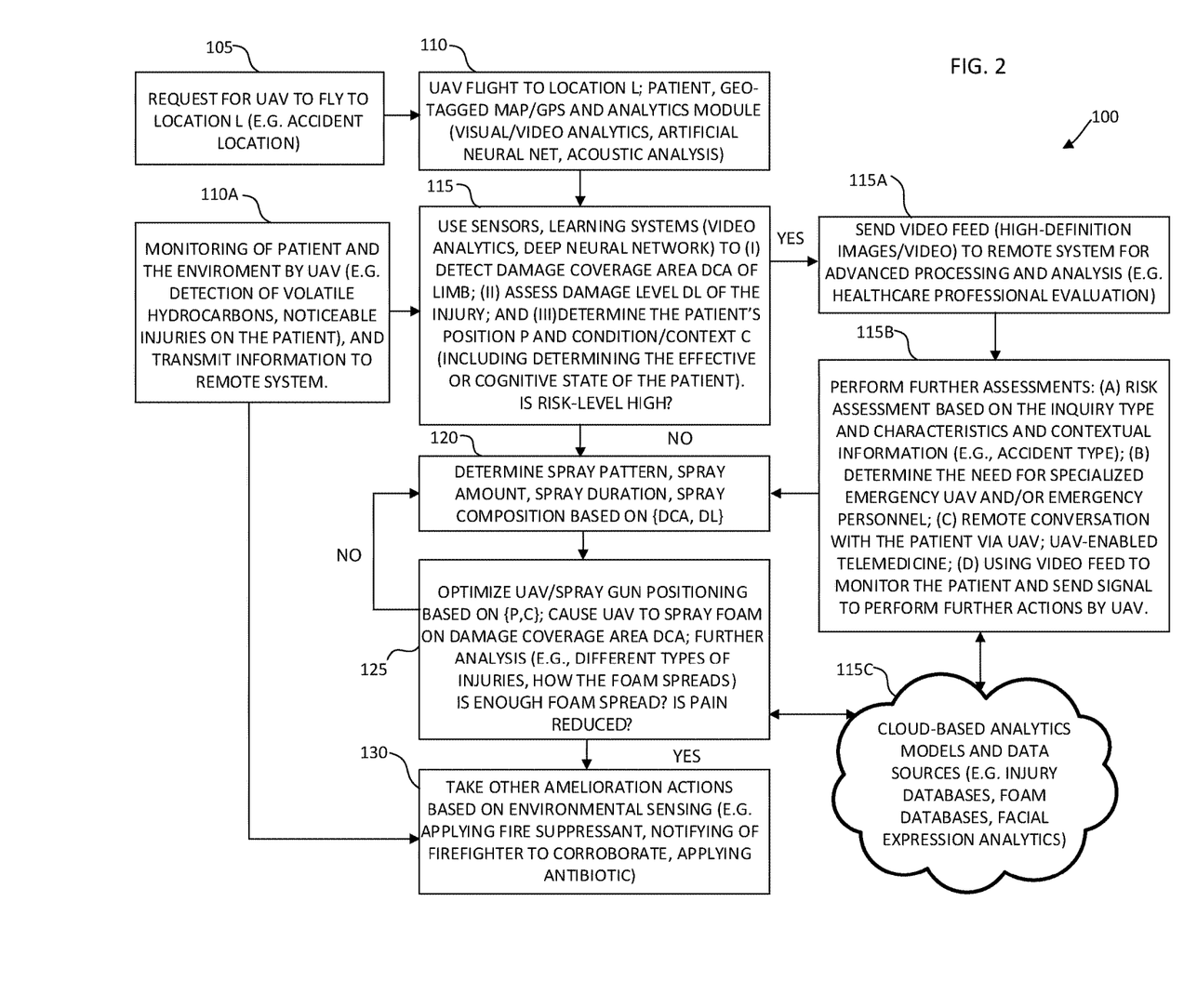
FIG. 2 is a flow chart showing the operation of a unmanned aerial vehicle to address detected injuries.

Referring to FIG. 2, a flow diagram 100 includes exemplary steps for employing a UAV 60 in determining whether ameliorative action is warranted and taking one or more actions based on the determination. A request is made in step 105 for the UAV 60 to fly to an accident location L. The request includes location information and may be made from a remote location or from the accident location L itself. In some embodiments, the patient 65 or a nearby person reports a possible limb injury at the location L. In response to the request, the UAV 60 is launched and flies to the location L. The patient is identified in step 110 using the sensors 62 and associated analytics in some embodiments or by a healthcare professional using a video and/or audio feed from the UAV in other embodiments. As discussed above, UAVs can be controlled using smartphones or other devices capable of wirelessly communicating with UAVs. As known in the art, the UAV can be controlled manually and/or autonomously, depending on the function to be performed. In some embodiments, the UAV is provided with location information and autonomously flies to the location L using, for example, the GPS system 79. In locations known to be potentially hazardous, radio transmitter(s) at or near the location L can facilitate UAV identification of the site and injured person or animal. The sensors 62 include an infrared sensor in some embodiments to facilitate location of the patient, particularly at night. The processor 74 (and/or 84) in some embodiments includes an image processor 208 operatively associated with a logic program including software routines and memory to perform multi-resolution image analysis. Such a program can be stored in the memory 78 or other electronic memory such as a distinct software module. Different resolutions of an image are checked to assist in object recognition. Initial resolution may be defined by detection of any large, presumably human object causing a change in a background environment. In some embodiments, the sensors 62 include a motion detector and a motion direction detection routine is performed. Edges of an image are computed and a saliency map (not shown) may be generated. Saliency map algorithms for facilitating analysis of an image are known to the imaging art. After successful localization and multiple segmentations, the saliency map blends edges to achieve intensity regions in the image. Highest peak values in the intensity regions have the highest probability of being the subject patient and are selected for further processing. Based on local edges and regional features, a refinement of an area of interest is determined for localization in a torso detection routine and a limb detection routine. Hand detection routines are disclosed, for example, in U.S. Pub. No. 2002/0090146 to Heger and U.S. Pat. No. 6,252,598 to Segen, both of which are incorporated by reference herein. Segmentation provides locations that are likely to include the targeted elements to be detected. This includes addressing illumination effects, positions, rotations, and distances of the patient from the UAV camera. Comparisons to normalized correlation models or templates are performed to find similar illuminations, distances, orientations etc. in order to facilitate the removal of the background from the image. To reduce illumination effects on the image, before classification, each sub-image is normalized with respect to brightness and contrast. This sub-image minus the background preferably has a fixed size. After successful localization, multiple segmentation hypotheses are created by an algorithm based on nonlinear projections onto a baseline image. The recognition system preferably employs a convolutional neural network classifier or other statistical classifier which identifies, for example, a human arm or leg, and a confidence value for the limb detected. Based on the confidence measure, the segmentation hypotheses with the highest overall confidence may be accepted or, if the confidence level does not meet a predetermined level of reliability, the UAV or a healthcare professional viewing the patient using the video feed from the UAV may issue instructions to the detected patient instructing him to (if possible) alter his position or orientation with respect to the camera so as to improve the quality of the image undergoing analysis. Such instructions can also be provided upon the first detection of human motion, possibly confirmed by an infrared sensor and/or acoustic analysis, at the location L so that the patient can assume a position or be assisted to a position that is conducive to limb detection and subsequent foam splint application. By incorporating an analytics module 64 within the UAV, identifying a patient at the location L becomes possible even where the patient cannot be found using high definition images transmitted by the UAV to a remotely located health care professional. In some embodiments of the process 100, step 110 includes use of a unique identification such as a bar code, color pattern, RFID tag signal, or other indicia applied to the patient at the location L that is electronically detected by the UAV. Facial recognition software may also be incorporated within an analytics module to facilitate patient identification based on the images obtained by the UAV. Facial expression software is further included in some embodiments and is used for assessing the emotional state of the patient 65 in step 115 as described below. Facial recognition and facial expression software is commercially available and continues to be developed. Raw facial expression data obtained from a webcam or other imaging device may, for example, be transmitted by the UAV 60 to the device 80 for importation into, for example, a statistical analysis processing module or analyzed within the UAV itself or a cloud-based system. Statistics packages such as IBM's SPSS Statistics are among those than may be used for interpreting facial recognition and facial expression data. Classification algorithms translate the facial features into emotional states and/or other metrics.

Step 110A involves the use of UAV sensors 62 to monitor the identified patient and the surrounding environment at the location L. Noticeable injuries on the patient can be detected in this step. A digital imaging device on the UAV can be employed for obtaining high definition images of the injuries that are analyzed by the UAV as part of step 115 or by a remote system. Other sensors are alternatively or additionally employed in combination with the digital imaging device. In some circumstances, injuries can be detected by a remote healthcare professional based on the video feed from the UAV or audio input from the patient speaking to the UAV at the location L. Limb dislocation or deformation are among the symptoms of an injury that may be diagnosed by a healthcare professional having access to the video feed or results of 3D image analysis. Environmental conditions, such as the presence of gasoline, damaged vehicle(s), or other noticeably injured persons are among the other conditions at the location L that can be detected and possibly be factored into the decision as to whether the UAV is to take ameliorative action with respect to the identified patient. The sensors 62 include chemical sensors in some embodiments of the UAV that detect gasoline and/or other volatile substances. Electrochemical gas detectors, infrared point sensors and infrared image sensors are among the types of chemical sensors that can be incorporated within the UAV for detecting volatile hydrocarbons.

Step 115 involves using analytics to interpret the data obtained from the sensors 62 for determining the position P of the patient (to the extent such position has not been determined in step 110), UAV detection of the damage coverage area DCA of the patient's limb(s) or torso, assessment of the damage level DL by the UAV, and assessing the overall patient condition C (including the patient's cognitive or emotional state) of the patient. Pattern recognition and machine learning facilitate the interpretation of raw data in a variety of applications and can be applied to at least steps 110 and 115 as described herein. Assessment of the damage level DL may determine, for example, whether the patient's limb is bruised or broken. Such information allows determination of whether the risk level is low and therefore conducive to the application of a foam spray by the UAV to immobilize a limb or high and therefore requiring inaction or further processing. For example, the patient's injured limb may or may not be in a position conducive to the application of a foam splint by the UAV. As discussed above, image processing by the UAV and other data obtained by the sensors 62 and used by the UAV and/or a healthcare professional allow identification of a patient as well as identification of torso, limb and head areas. Damage to a part of a patient's body (damage area DA) is ascertained using video-analytics in some embodiments, including for example neural network classification to diagnose particular injuries and the level of such injuries. The UAV includes an xray back-scattering radiographic system in some embodiments that obtains images that are analyzed using such classification. Such images may include information related to the internal structure of the patient's limb (e.g. bone structure) or only the outer surface of the limb itself. Back-scattering allows observation of a patient's limb beneath layer(s) of clothing. Bone fractures are often accompanied by limb distortion, breaking of the skin, swelling and/or skin discoloration. Diagnosis is facilitated by detection of one or more of such conditions. While imaging of a bone itself would likely provide a diagnosis of both the damage area DA and damage level DL having the highest confidence level, it is not necessarily required in order for the UAV to diagnose the probability of a fracture or similar injury, such as a serious ligament injury or rupture. For example, the patient could communicate the presence of pain in an arm to a UAV that employs speech recognition software. If swelling and discoloration of the painful arm are also detected by a camera and/or back-scattering system using, for example, pattern recognition and/or image color recognition software, the confidence level of a fracture diagnosis is increased. In some embodiments, images of the arms and/or legs of a patient obtained by the UAV are compared with each other for differences in physical characteristics that may suggest an injury in one limb but not another. Upon analysis of the damage coverage area DCA, the damage level DL, the position P of the patient, the patient's condition C, and possibly additional factors, a risk level determination is made. The system 50 may use various online or offline injury databases (e.g. European Injury database (IDB)—international burn injury database (iBID), and/or injury databases from various healthcare facilities wherein an injury can be characterized by a type, shape, behavior, danger level, expansion capacity. Environmental context information can also be considered: e.g. weather, type of accident). Such databases can be used to build various learning models which can be deployed within the system to detect, classify and characterize injuries in realtime. Thus, during an emergency situation, visual analytics and/or deep neural net modules may be able to detect, classify, and further characterize injuries as observed by the UAV. Audiovisual information transmitted from the UAV to a remote healthcare professional can further assist in obtaining injury information.

If processing of the risk level factors discussed above by the UAV results in a determination that the risk level is high, the UAV takes no immediate action with respect to the patient. A high risk level may be based on one or more findings, such as the failure by the UAV to detect a damage area, an unfavorable position of the patient for the application of a foam splint, and/or evidence of the patient being in a disturbed or agitated state that would make the application of a foam splint by the UAV problematical. There may also be insufficient data that would allow the UAV to determine the correct foam spray composition. Risk level may alternatively be based on a combination of the findings in some circumstances where no single factor is sufficient to result in a "high risk" determination. The exemplary UAV 60 is configured to transmit high-definition images in step 115A and/or other data obtained by the sensors 62 to a remote system for further processing and analysis by a health care professional using the transmitter/receiver 72. The remote system includes the device 80 used for controlling the UAV in some embodiments, though data from the UAV can alternatively be sent to another remote site or multiple sites configured for receiving the data. Step 115B is then conducted at the remote site. This step involves performing further assessment including i) risk assessment based on the inquiry type and characteristics, using online or offline databases (e.g. IDB, iBID) in some embodiments as well as contextual information (e.g. accident type); ii) determining the possible need for specialized emergency UAVs and/or emergency personnel; iii) remote conversation/data exchange with the patient or person(s) near the patient via UAV-enabled telemedicine; iv) monitoring the condition of the patient using a videofeed from the UAV and optionally signaling the UAV to perform further actions from a remote site. Such additional analysis, possibly aided by image enhancement of the images obtained by the UAV, may increase the confidence level of a diagnosis, thereby reducing the risk level and causing a signal to be sent to the UAV 60 with instructions relating to the application of a foam splint to the patient's limb. Such instructions, which may be digitally encoded, control: 1) the distance between the UAV and the patient, 2) the dispensing of foam on a limb, 3) movement of the UAV and/or foam nozzle during the application of foam. In some embodiments, the composition of the applied foam is also controlled.

Analytics models and data sources are stored on a cloud in some embodiments, and are accessible by one or more of the UAV 60, the remote device 80, or a remotely located healthcare professional. Injury databases, incident databases, location databases, historic feedback, foam databases (for example recommended foam patterns, amounts, compositions) are among the stored data in some embodiments. As shown in FIG. 2, step 115C involves the accessing of cloud-based analytic models and/or data sources by a remote system in the processing of information received from the UAV 60. In some embodiments, the UAV 60 accesses the cloud computing environment directly. Cloud computing is described in further detail below.

Based on the determinations made by the UAV and/or remote system as described above, with possible reference by either to cloud-based analytics models or data, a determination is made in step 120 with respect to one or more of a foam spray pattern, a foam spray volume to be dispensed by the UAV, spraying duration, and/or foam composition. Such determination is based on the damage coverage area DCA and the damage level DL. The use of a polyurethane foam for the purpose of forming a rigid or semi-rigid structure such as a splint may involve the mixing of precursor materials during the course of application to a patient. The mixed materials rapidly cure to form the splint. The payload 66 in some embodiments of the UAV 60 accordingly includes pressurized containers containing each precursor material. A two-component foam discussed in the art for forming foam splints includes a polyisocyanate component and a polyol component that are mixed in or near a nozzle to form a polyurethane foam. Such foams are commercially available and are also used in the construction industry. The foam density is controlled by changing the amount and/or type of blowing agent, for example a hydrofluorocarbon that enhances frothing. Water is optionally employed in the blowing agent. Lower water contents are associated with foams of greater rigidity. The UAV may further include a heater for keeping the payload, including the foam precursor materials, sufficiently warm when attending to a patient in cold outdoor temperatures. The UAV dispenser 68 is in the form of one or more dispensing guns and associated nozzles in some embodiments. Different foam precursors and/or spray patterns may be associated with each of the dispensing guns. Disposable nozzles are preferably employed to allow the operator to change nozzles after each use or to select nozzles having particular spray patterns considered appropriate for one or more situations. Nozzles may, for example, have circular ends, flared ends for producing a fan-shaped spray, or rectangular ends. Foam dispensing guns and associated nozzles for dispensing two-component polyurethane foams in situ are known to the art and continue to be developed. The components of a two-component polyurethane foam are typically mixed within the dispensing nozzle. While two-component polyurethane foams are employed in some embodiments for forming a splint to immobilize an injured limb, it will be appreciated that foams having compositions other than those disclosed herein may be employed, provided they have the abilities to form an effective splint. As known in the art, the foam chosen for forming a splint in situ should be relatively quick-setting and should not generate temperatures above the range that is comfortable for a patient. In one or more embodiments, the applied foam sets sufficiently within a minute or two in order to stabilize an injured limb or associated extremity such as a hand or foot.

Step 125 includes controlling the position of the UAV with respect to the injured limb of the patient and spraying the damage coverage area (DCA) with the foam. It further includes discontinuing spraying after a set time has elapsed, when a decision is made is discontinue spraying automatically using visual analytics, or pursuant to instructions received by the UAV from the patient or healthcare professional. In some embodiments, spray duration is set in step 120 and spraying is discontinued after a set time has elapsed. If the dispensing rate of the foam material is known, the spray duration also determines the amount of foam material that is dispensed. In other embodiments of the method, images of the sprayed area taken by the UAV, possibly in combination with additional factors, are analyzed to determine whether there is sufficient foam coverage of the damaged area. In some embodiments, the processing of visual sensor information, possibly in combination with flow rate, spraying time and/or other factors, using for example a deep neural network, results in the assignment of a confidence score that a foam splint has the desired size (coverage area) and thickness to be effective. Once an appropriate confidence level has been reached that sufficient foam has been applied to form an effective splint, a signal is sent to the actuator for the dispenser 68 (e.g. foam dispensing gun) and foam application is discontinued by the UAV. An analytics module may be contained within the UAV or a cloud-based system that includes a model configured for analyzing images of the foam splint as it is formed and takes time, flow rate, and/or other available information such as the size of the patient and the foam composition in controlling the application of foam. Feedback from the patient may further be included if available in determining whether to continue spraying the injured limb. Such feedback may relate to whether the damaged area DA is sufficiently covered and/or whether the patient has experienced a reduction in pain. Speech recognition software is employed by the UAV in some embodiments for facilitating operation of the UAV during the application of a foam splint. The UAV is configured to respond to voice commands or other patient feedback (e.g. gestures) in such embodiments by, for example, changing the UAV elevation or its flight path above the patient, discontinuing foam application, or initiating foam application. The use of a UAV having hovering capability is preferred for controlling the formation of the foam splint.

Control of the UAV during step 125 may be exercised by remotely located healthcare professionals using a device 80 as described above in some embodiments. A high-definition video feed to a healthcare facility or cloud-based system accessed by a healthcare professional is employed to observe the spraying operation and splint formation. Based on such observations, the UAV and/or spraying equipment is maneuvered with respect to the patient to form a splint having the desired configuration and properties. In some embodiments, the UAV is positioned just above the patient and traverses an injured limb while the foam spray is applied. In other embodiments, the UAV is maintained (hovers) in a stationary position just above the patient and the spray gun or nozzle is articulated to cover the damage coverage area DCA with foam. Such UAV/spray gun movements and foam spray emission can be controlled by a remotely located healthcare professional, by the patient, or the UAV itself. The spray pattern determined in step 120 is stored in the UAV memory 78 or the remote device memory 86 in some embodiments such that the UAV automatically forms a foam splint according to the spray pattern through movement of the UAV and/or spray nozzle(s) with respect to the injured limb. The spray pattern and/or the amount of foam dispensed can be adjusted based on feedback from the patient and/or further analysis of the visual images obtained by the UAV. The foam splints formed by the UAV do not envelope the entireties of the damaged areas in at least some embodiments so that possible further swelling of the injured limb is allowed to minimize pain. The splints are formed either on the patient's skin or over the patient's clothing. In some embodiments, the UAV 60 is employed to form a spine board by applying foam to the back of a patient followed by contacting the foam with a board before the foam sets. A person at the injury location L would need to assist the patient with the positioning of such a board.

Step 130 involves taking further ameliorative action(s) using the UAV 60 or other UAVs. The action(s) are responsive to the detection of further injuries such as traumatic vascular injuries on the patient and/or environmental factors potentially affecting the injured patient. In one exemplary embodiment, the UAV 60 sensors include a volatile hydrocarbon sensor that detects gasoline at the location L. This information is possibly supplemented by data received from other UAV sensor(s) such as visual data obtained from a digital camera that affect the confidence level of a possible decision to take further ameliorative action. Ameliorative actions following the detection of a gasoline spill include the application by the UAV 60 or another UAV of a fire suppressant at the location L and/or notification of firefighters of the detected issue(s) at the location L. In a second exemplary embodiment, an open wound on the patient is detected by the UAV. Prior to or following formation of the foam splint, the UAV 60 or another UAV carrying the appropriate payload administers a spray containing an antibiotic, a blood clotting formulation, an anesthetic, or other material considered likely to benefit the patient.

It will be appreciated that, while the UAV 60 is capable of forming foam splints for immobilizing a patient's limbs and/or back, it may alternatively be deployed for other purposes in which the application of a foam spray would be beneficial. For example, the foam could be applied to insulate downed electrical wires, plug leaks in tanks or lines, provide a protective covering over jagged metal or broken glass to facilitate rescue, to make a damaged infrastructure safer for first responders, or to cover potentially hazardous materials at the location L. The UAV 60 may be part of a system including a plurality of UAVs for responding to natural disasters, accident scenes, or other situations involving a large number of injuries. The system may coordinate a group of UAVs attending injured patients, optimizing and prioritizing application of foam and/or other agents, thereby performing triage. For example, the needs of each injured person at an accident scene can be assessed and prioritized where the supply of foam and/or other agent is limited. The system may include specialized UAVs for assessing injuries and other UAVs configured for addressing the assessed injuries through the application of foam and/or other agents such as antibiotics, anesthetics or hemostatic compositions. It will accordingly be appreciated that, in some embodiments, a first UAV is used to obtain data relating to the physical characteristics of a patient while a second UAV is used to take ameliorative action with respect to the patient based on assessments based on the physical data. A smaller, lighter UAV may accordingly be used to obtain visual images and/or sound data. Larger, heavier UAVs carrying payloads of foam-creating materials or other treatment materials would then be used to treat the patient. A UAV that performs both functions could, in real-time, detect and then quickly help the patient, particularly is diagnosis if conducted using analytic software as opposed to manual examination by a healthcare professional who may not be immediately available. There would accordingly be very little delay between detection and aid rendered to the patient.

Given the discussion thus far and with reference to the exemplary embodiments discussed above and the drawings, it will be appreciated that, in general terms, an exemplary method for assisting an injured patient includes obtaining an unmanned aerial vehicle 60 that includes a payload 66 including one or more materials for forming a polymer foam, a dispenser 68 such as a spray gun with attached nozzle for dispensing the one or more materials in the payload, and one or more sensors. The unmanned aerial vehicle is flown to a location L in proximity to a patient and the patient 65 is identified at the location L. Foam is dispensed on a limb of the patient using the dispenser by dispensing the one or more materials in the payload, thereby forming a foam splint. Physical characteristics data relating to the patient based on an output of the one or more sensors is obtained in one or more embodiments. Based on the physical characteristics data, it is determined whether it is likely that a limb of the patient is injured. The one or more materials for forming the polymer foam on the patient are dispensed if it is determined that the limb of the patient is likely injured to form a foam splint. The physical characteristics data may be based on digital images of the limb which are assessed remotely in some embodiments. The digital images, which may be included in audiovisual transmissions by the UAV, include external features of the limb and/or internal features of the limb. In some embodiments, at least one of the sensors 62 is an acoustic sensor and the method further includes detecting sounds at the location using the acoustic sensor, analyzing the detected sounds using speech recognition software, and actuating the dispenser based on the analysis of the detected sounds by the speech recognition software. The method may further include obtaining digital images of the foam splint from the one or more sensors 62 during the forming of the foam splint, and discontinuing forming the foam splint based on the digital images. The step of determining whether it is likely that a limb of the patient is injured further includes using a neural network classification to diagnose a particular injury from the physical characteristics data in some embodiments. The decision as to whether to dispense foam from the UAV involves consideration of images of a patient's limb, the position of the patient and/or the patient's possibly injured limb, and the patient's emotional state as determined using facial expression software in some embodiments. The patient's indication of pain, which may be obtained via speech recognition processing, may further influence the decision to dispense foam on an injured limb. The electronic processing of the data obtained by the sensors, either by the UAV or at a remote location, facilitates prompt decision-making as to whether or not a foam splint is to be formed. In some situations, electronic processing using convolutional neural network classifiers or other statistical classifiers, facial expression modules, and/or other computer-controlled techniques to determine the patient's position, injuries, and cognitive state do not allow a high confidence decision to be made. In such situations, high definition images of the patient and location can be transmitted by the UAV to a healthcare professional for review. The healthcare professional could confer with the patient via the UAV, which in some embodiments includes acoustic detectors and speakers for transmitting sound. In some embodiments, speech recognition technology enables the patient or a nearby individual to at least partially control the UAV and its dispensing of foam on an injured limb.

A system for assisting an injured patient includes an unmanned aerial vehicle 60 including one or more materials for forming a polymer foam, a dispenser 68 for dispensing the one or more materials in the payload, and one or more sensors 62. A processor is configured for processing outputs from the one or more sensors to: 1) identify a patient at a location using the one or more sensors; 2) obtain physical characteristics data relating to the patient based on an output of the one or more sensors, and 3) determine whether it is likely that a limb of the patient is injured based on the physical characteristics data. The UAV further includes an actuator 70 that, in some embodiments, is controlled by the processor. The actuator 70 is provided for actuating the dispenser 68. The sensors include an image sensor and the UAV includes a transmitter 72 configured for transmitting data obtained by the image sensor. The sensors further include an acoustic sensor, the transmitter being further configured for transmitting data obtained by the acoustic sensor. Acoustic sensors may be used to detect environmental conditions at the injury location L and/or to permit audio communication between the patient and the UAV. The UAV includes a facial expression module configured for analyzing data obtained by the image sensor in some embodiments, thereby facilitating identification of emotional states. The image sensor can be configured for detecting visible light, backscattered xrays, infrared radiation, and/or other radiation facilitating analysis of the patient or patient injuries. In some embodiments, the UAV sensors further include a chemical sensor for detecting volatile hydrocarbons.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The above-described embodiments are intended to be illustrative only. Other embodiments may, for example, utilize different materials and processing steps from those expressly set forth above to achieve embodiments falling within the scope of the present disclosure. These many alternative embodiments will be apparent to one having ordinary skill in the relevant arts.

All the features disclosed herein may be replaced by alternative features serving the same, equivalent, or similar purposes, unless expressly stated otherwise. Thus, unless expressly stated otherwise, each feature disclosed is one example only of a generic series of equivale The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "above" and "below" are used to indicate relative positioning of elements or structures to each other as opposed to relative elevation. It should also be noted that, in some alternative implementations, the steps of the exemplary methods may occur out of the order noted in the figures. For example, two steps shown in succession may, in fact, be executed substantially concurrently, or certain steps may sometimes be executed in the reverse order, depending upon the functionality involved.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Any element in a claim that does not explicitly state "means for" performing a specified function or "step for" performing a specified function is not to be interpreted as a "means for" or "step for" clause as specified in AIA 35 U.S.C. § 112(f). In particular, the use of "steps of" in the claims herein is not intended to invoke the provisions of AIA 35 U.S.C. § 112(f).

What is claimed is:

1. A method of operating an unmanned aerial vehicle, comprising:
    obtaining, by the unmanned aerial vehicle, location information indicating a location, the unmanned aerial vehicle comprising:
        a payload including one or more materials for forming a polymer foam;
        a dispenser for dispensing the one or more materials in the payload; and
        one or more sensors;
    flying the unmanned aerial vehicle to the location;
    identifying a target individual requiring stabilization at a position within the location using the one or more sensors, wherein the target individual is a patient;
    detecting, using the one or more sensors, a condition of the target individual requiring stabilization;
    obtaining physical characteristics data relating to the patient based on an output of the one or more sensors,
    determining whether a limb of the patient is injured based on the physical characteristics data;
    determining an amount of the one or more materials of the payload to be dispensed on the limb of the patient based on the physical characteristics data;
    determining a pattern in which the one or more materials of the payload are to be dispensed on the limb of the patient by analyzing the physical characteristics data and a type of the physical characteristics data;
    dispensing the one or more materials for forming the polymer foam on the target individual to form a foam structure while maneuvering the unmanned aerial vehicle to define a shape of the foam structure and causing the formation of the foam structure according to the pattern by maneuvering the unmanned aerial vehicle while dispensing the one or more materials, the maneuvering being based on an analytics model, wherein the dispensing the one or more materials is based on a determination that the limb is injured; and
    discontinuing the dispensing the one or more materials in the payload once the amount of the one or more materials of the payload have been dispensed.

2. The method of claim 1, wherein the physical characteristics data is based on digital images of the limb.

3. The method of claim 2, wherein the digital images include external features of the limb.

4. The method of claim 2, wherein the digital images include internal features of the limb.

5. The method of claim 2, wherein at least one of the sensors is an acoustic sensor, further including detecting sounds at the location using the acoustic sensor, analyzing the detected sounds using speech recognition software, and actuating the dispenser based on the analysis of the detected sounds by the speech recognition software.

6. The method of claim 1, further including:
obtaining the visual sensor information of the foam structure from the one or more sensors during the forming of the foam structure, detecting a completion of the foam structure based on the visual sensor information, and discontinuing forming the foam structure based on the visual sensor information.

7. The method of claim 6, wherein the detecting the completion of the foam structure is based on one or more of a volume of the dispensed materials and an analysis of the digital images.

8. The method of claim 1, wherein determining that the limb of the patient is injured further comprises using a neural network classification to diagnose a particular injury from the physical characteristics data.

9. The method of claim 1, further including transmitting signals including the visual sensor information from the unmanned aerial vehicle to a remote site, displaying one or more visual images based on the visual sensor information at the remote site, and controlling the unmanned aerial vehicle from the remote site based on the one or more visual images.

* * * * *